United States Patent [19]

Prass et al.

[11] Patent Number: 5,563,707
[45] Date of Patent: Oct. 8, 1996

[54] INTERFERENCE ENHANCED OPTICAL SENSOR FOR DETECTING CHEMICAL SPECIES

[75] Inventors: Werner Prass, Mainz; Thomas Stehlin, Hofheim/Taunus, both of Germany; Yuan Liu, Kawagoe, Japan; Shizuo Ogura, Tsurugashima, Japan; Kenji Motosugi, Kawagoe, Japan; Akihiko Tokida, Kawagoe, Japan; Tetsu Yamamoto, Kawagoe, Japan

[73] Assignee: Hoechst Aktiengesellschaft, Frankfurt, Germany

[21] Appl. No.: 467,935

[22] Filed: Jun. 6, 1995

Related U.S. Application Data

[63] Continuation of Ser. No. 152,400, Nov. 15, 1993, abandoned.

[30] Foreign Application Priority Data

Nov. 17, 1992 [JP] Japan ................... 4-307291

[51] Int. Cl.⁶ ........................................ G01B 9/02
[52] U.S. Cl. ................ 356/361; 356/345; 356/128
[58] Field of Search .................... 356/128, 361, 356/369, 381, 448, 345

[56] References Cited

U.S. PATENT DOCUMENTS

| Re. 33,064 | 9/1989 | Carter et al. ............ 356/414 |
| 4,525,376 | 6/1985 | Edgerton . |
| 4,641,524 | 2/1987 | Tarvin . |
| 4,708,941 | 11/1987 | Giuliani ................. 356/445 |
| 4,910,998 | 5/1990 | Willis et al. . |
| 4,983,823 | 1/1991 | Isobe ..................... 356/369 |
| 5,153,666 | 10/1992 | Pawliszyn .............. 356/128 |
| 5,155,555 | 10/1992 | Wetegrove ............. 356/381 |
| 5,165,005 | 11/1992 | Klainer et al. ......... 356/128 |
| 5,187,363 | 2/1993 | Birkle . |
| 5,218,212 | 7/1993 | Sato et al. ............. 356/412 |

FOREIGN PATENT DOCUMENTS

| 02282009 | 9/1988 | European Pat. Off. . |
| 0536656 | 10/1992 | European Pat. Off. . |
| 2419069 | 6/1975 | Germany . |
| 3832185 | 9/1988 | Germany . |
| 4008486 | 4/1990 | Germany . |
| 2185579 | 7/1987 | United Kingdom . |
| WO83/02327 | 7/1983 | WIPO . |

OTHER PUBLICATIONS

English Abstract, JP-OS-No. 74485.
English Abstract, JP-OS-No. 96846.
English Abstract, JP-OS-No. 96847.
Brown et al., AIAA Paper No. 74–114, "Joint Conference on Sensing of Environmental Pollutants". Nov. 1971.
English Abstract, JP-OS-No. 238746.
English Abstract, JP-OS-No. 47531.
Mitschke, F., *Fiber-optic sensor for humidity*, Optical Letters, vol. 14, No. 17 (1989) pp. 967–969.
Sensors and Actuators, (1982/83), pp. 79–88, "Gas Detection by Means of Surface Plasmon Resonance".
English Abstract, U.S. Appln. No. 259556.
English Abstract, JP-OS-No. 77651.
English Abstract, JP-OS-No. 190142.
English Abstract, Jp-OS-No. 133900.
English Abstract, JP-OS-No. 142152.

*Primary Examiner*—Samuel A. Turner
*Attorney, Agent, or Firm*—Curtis, Morris & Safford, P.C.

[57] ABSTRACT

An optical sensor for detecting gaseous or liquid chemical species including a sensing element having a flat light reflecting substrate and one or more transparent thin films which are organic or inorganic films or high-polymer films and are formed on the substrate. The detection of the gaseous or liquid chemical species is effected by measuring a change in the light reflection characteristic of the sensing element based on swelling of the thin film or a change in its thickness or refractive index or changes in both parameters.

12 Claims, 8 Drawing Sheets

INTERFERENCE ENHANCED OPTICAL SENSOR FOR DETECTING CHEMICAL SPECIES

This application is a continuation of application Ser. No. 08/152,400, filed Nov. 15, 1993, now abandoned.

BACKGROUND OF THE INVENTION

This invention relates to an optical sensor for detecting chemical species. More particularly, the invention relates to an optical sensor that relies upon interference enhanced reflection (hereunder abbreviated as IER) for detecting chemical species using reflected light from a thin organic or high-polymer film that functions as a sensing element. The thin film either reacts with or adsorbs gaseous or liquid chemical species.

Various types of optical sensors are known that rely upon the reflection of light for operation. One of the most recent examples is the proposal by Gauglitz et al., who reported a method of reflection spectroscopy for detecting gases or solvents using the swelling of polymer films (GIT Fachz. Lab., 7, 889, 1990). This method uses a white light source and a spectrometer for analyzing the spectral reflectance; hence, the equipment for implementing this method is bulky with the additional need to use an optical filter and other peripheral parts.

European Patent Publication No. 0 282 009 A2 teaches a fiber optical detector that makes use of the change in reflectance due to the interaction with hydrocarbons. The operating principle of the detector described in the publication is that the refractive index of the cladding will change in the presence of hydrocarbons thus causing changes in optical losses.

Nylander et al. discussed a gas sensor that relied upon surface plasmon resonance for operation (Sensors and Actuators, 3, 79–88, 1982). The conditions for resonance of surface plasmons that occur in the sensor are largely dependent on the optical parameters of the polymer film used in the sensor, which in turn will vary upon exposure to the vapors of organic matters. U.S. patent application Ser. No. 259,556 (Oct. 18, 1988) teaches a fiber optic sensor for chemical species that has a thin metal film formed at an end of the optical fiber. The operating principle of this sensor is as follows: when the thin metal film is brought into contact with a chemical species, the thickness of the film and, hence, its reflection characteristics will vary.

Butler reported an interference sensor that had a polymer film formed at an end of a multimode optical fiber. The operating principle of this sensor is that when the polymer is brought into contact with a chemical species, it will swell to thereby change the reflecting property of the fiber and at which the polymer is formed. A problem with this sensor is that it is not easy to form a thin polymer layer at an end of the optical fiber.

Japanese Laid-Open Patent Application No. 77651/1992 describes a fiber optic sensor of chemical species that uses a sensing membrane containing both a dye and a chemical species sensitive compound. The operating principle of this sensor is that when the chemical species sensitive compound binds with the chemical species to be detected, the sensing membrane will experience a change in light reflectance or color.

The fiber optic sensor described above have one problem in common; that is, the change in reflectance that can be observed is so small that no satisfactory sensitivity is attainable, whereby the dynamic range of the sensors is limited.

Japanese Laid-Open Patent Application No. 19042/1922, 133900/1993 and 142152/1994 disclose a chemical sensor for ammonia and amine which uses a conductive polymer thin film on a transparent conductive substrate. The reflectance of the film changes when it is contacted with a chemical substance to be detected. However, the sensor is based on a simple reflection measurement that does not utilize the optical interference techniques. The present invention uses the IER method that specifically relies on optical interference from a thin structure. U.S. Pat. No. 4,641,524 teaches an optical humidity sensor that is equipped with a mirror having a layer of a porous water-absorbing dielectric material. U.S. Pat. No. 4,525,376 teaches a thickness regulator that relies upon wavelength-dependent reflection for monitoring a silicon layer on a substrate.

Japanese Laid-Open Patent Application No. 19142/1992 describes an ammonia sensor which utilizes a change in light reflectance on the surface of a polymerized film having an electrically-conductive polymer. However, this sensor does not exhibit quick response and thus a sensor with quicker response has been demanded.

An object of the present invention is to provide a sensor that has a higher sensitivity and selectivity, that features quick response, and that is small enough to be constructed easily.

According to the present invention, there is provided an optical sensor for detecting gaseous or liquid chemical species that includes a sensing element having a thin film and a means of measurement by IER.

The present invention also provides an optical sensor that uses a thin organic or inorganic film or a thin high-polymer film as the thin film in the sensing element.

The present invention further provides an optical sensor that is capable of detecting a single or a plurality of chemical species as distinguished from each other by measuring the change in the relative intensity of reflected light or the response on the basis of the swelling of the thin film or the changes in its optical parameters.

The present invention also provides an optical sensor that comprises a series of sensing elements which are made of similar or dissimilar materials for achieving simultaneous detection of different chemical species, increasing the precision of identification, and correcting background effect.

The present invention further provides an optical sensor that accomplishes not only quick response but also high sensitivity and broad dynamic range by selecting proper substrate materials, optimal values for the thickness of the thin film in the sensing element and the angle of incidence of light.

The present invention also provides an optical sensor incorporated in a detection system that comprises a light source, a polarizer, optical paths for reference light and signal light, photodetectors, and electronic circuitry.

BRIEF DESCRIPTION OF THE DRAWINGS

FIG. 9A shows a cross section of a series of sensing elements and photoreflectors for simultaneous detection of different chemical species; and FIG. 9B shows a plane view of a single photoreflector.

The sensing element that can be used in the present invention may comprise a flat reflecting substrate and one or more transparent thin organic or polymer films formed on that substrate. The thin film is of such a nature that it either reacts with or absorbs or adsorbs a certain chemical species. Alternatively, the thin film may react with or absorbs or adsorbs more than one chemical species that fall within a certain category. The thin film need not be made or organic or polymer materials and it may be made of other materials such as organometallic compounds and inorganic materials. The substrate for supporting the thin film is preferably flat enough to reflect incident light. Materials that can be used to make the substrate include, for example, highly reflective materials such as metals or semiconductors like silicon, or a reflecting film on substrate, and transparent glass. A high sensitivity and a broader dynamic range are attained if the substrate is highly reflective.

In accordance with the present invention, gaseous or liquid chemical species are detected by measuring the change in the reflection characteristics of the sensing element on the basis of the physical change such as swelling of the thin film or the change in its thickness and/or refractive index. As already mentioned, the thin film reacts or otherwise interacts with one or more chemical species that fall within a certain category. As a result of such interaction, the thin film will swell or experience other changes, which in turn cause changes in the optical parameters (i.e. the thickness and refractive index) of the thin film. Since these various changes cause corresponding changes in the optical properties of the thin film, one can detect gaseous or liquid chemical species by measuring the change in the reflection characteristic of the thin film, or the sensing element which includes it. In the present invention, such change in the reflection characteristic of the thin film is measured by IER. In a preferred embodiment of the present invention, the change in the product of the thickness and refractive index of the thin film that occurs when it reacts with or absorbs or adsorbs a chemical species is detected through measurement by IER.

IER is a method that utilizes the optical interference characteristics of the thin film. Light reflected from the surface of the thin film will interfere with light reflected at the interface between the thin film and the substrate. The intensity of reflected light is largely dependent on the thickness and refractive index of the thin film. Thus, the change in either the thickness of the thin film or its refractive index or the changes in the both factors will appear as the change in the intensity of reflected light. Even in the case where a plurality of swollen thin films behave differently, the degrees of swelling of the respective thin films can be easily identified on the basis of the changes in the intensity of reflected light from the films. In short, the physical changes that occur in the thin film and which are used in IER are the changes in the thickness and/or refractive index of the film. In the present invention, the IER technique is used to check for the presence of a chemical species and/or detect its quantity as a function of the intensity or reflected light.

The present invention also makes it possible to detect a plurality of chemical species as distinguished from each other by measuring the change in the intensity of reflected light or response time that occurs as a result of the swelling of the thin film or the change in its optical parameters (e.g. its thickness and refractive index). Stated more specifically, the interaction between the thin film and the chemical species to be detected varies with the types of the thin film and the chemical species and, hence, the intensity of reflected light that occurs as a result of the interaction will also vary with the specific combination of the thin film and the chemical species. The same is true of response time, which varies with the degree of interaction between the thin film and the chemical species. Thus one can distinguish between several chemical species on the basis of relevant information such as the change in the intensity of reflected light or response time. In order to detect and identify a plurality of chemical species simultaneously in the present invention, it is preferred to use a series of sensing elements that are made of similar or dissimilar materials.

The sensor of the present invention may be designed as a system which includes not only the sensing element described above but also the necessary parts for constructing an IER measuring means, such as a light source, a polarizer, optical paths for reference and signal light, photodetectors and electronic circuitry. The sensing element received light from the light source and issues reflected light. The photodetectors receive the light reflected from the sensing element and the light travelling in the optical path for reference light and produce electric signals as a function of the intensity of light. The electronic circuitry checks for the presence of a chemical species and/or calculates its quantity by making comparison between electric signal $I_S$ which is indicative of the intensity of reflected light from the sensing element and electric signal $I_R$ which is indicative of the intensity of reference light. The electronic circuitry having this function may be equipped with an additional circuit for producing an output signal that responds linearly to the quantity of the chemical species to be detected. If the sensor of the present invention is to detect the presence of toxic, combustible or flammable gases, vapors or solvents, the signal generated by the electronic circuitry may be used to trigger an alarm and/or perform on-off control over various switches or pipelines. If desired, means may be added to control the equipment or process under consideration. Adopting an optical detection means, the sensor of the present invention is effectively protected against explosion and, hence, is particularly useful for the purpose of detecting the leakage of explosive or flammable substances.

For these reasons, the sensor of the present invention is applicable to various uses over a broad range including process control, quality control, environmental monitoring, and detection of gas or liquid leakage.

One of the most appropriate use of the sensor of the present invention is in selective identification of fuel types at gas stations, especially for distinguishing between gasoline and diesel oil which are frequently confused by servicemen. Since the sensor of the present invention is explosion-proof, it can be used safely even at sites such as gas stations that handle flammable or combustible substances. The applicability of the sensor was fully demonstrated within the temperature range of −40° to 80° C. which is generally held to be necessary for the purpose of detecting gasoline as distinguished from diesel oil. In addition, it is possible to assemble a sensor system using a plurality of sensors according to the present invention.

Figure 1:
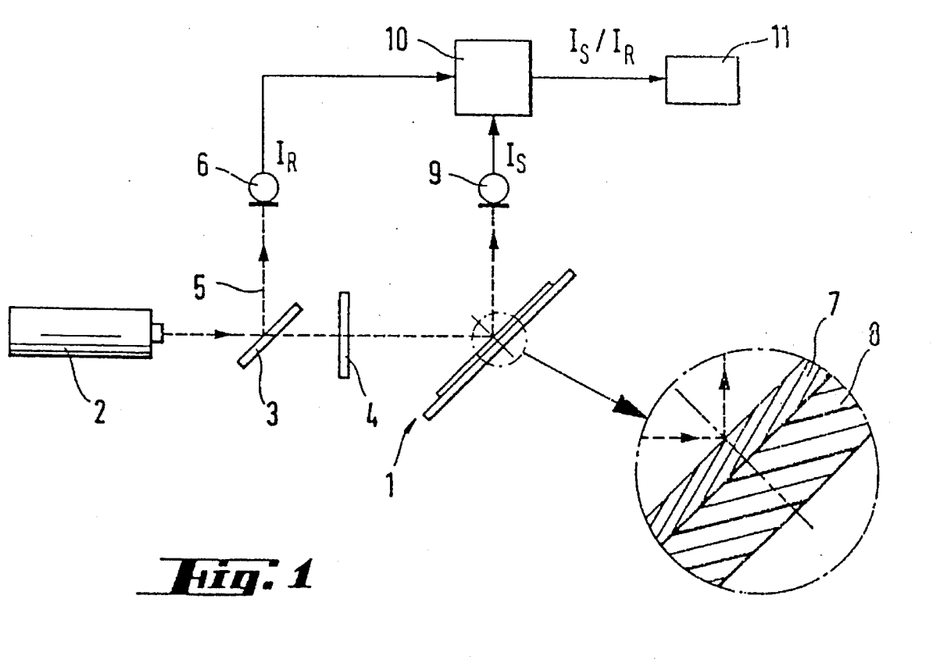
FIG. 1 is a diagram showing the general layout of IER equipment.

An embodiment of the present invention is shown in FIG. 1. Light to be incident of the sensing element indicated by 1 is issued from a light source 2, which may be a laser or a light-emitting diode (LED). The laser may be a He—Ne laser. The light issued from the light source 2 is divided into two beams by a beam splitter 3; one of the beams is admitted into a polarizer 4 and the other beam travels in an optical path for reference light 5 and reaches a photodetector for reference light 6, where it is converted to an electric signal. The light passing through the polarizer 4 is polarized in a direction normal to the plane if incidence of the sensing element 1. The polarized incident light is reflected not only on the surface of the sensing element 1 (i.e., the surface of a thin film 7) but also at the interface between the thin film 7 and a substrate 8. The light reflected from the surface of the thin film 7 interferes with the light reflected at the interface and the resulting light travels to a photodetector for signal light 9, where it is converted to an electric signal. The photodetectors may be photodiodes and they generate electric signals in proportion to the intensity of the light they receive. The photodetector 6 for reference light generates electric signal $I_R$ and the photodetector 9 for signal light generates electric $I_S$; these electric signals are supplied to electronic circuitry 10, which outputs the ratio between the two electric signals $(I_S/I_R)$ as a measurement signal. The thus produced output signal is recorded on a suitable recording means 11.

As a light source of the present invention can be used lasers, laser diodes (LD), light emitting diodes (LED) and incoherent light sources such as lamps. In addition, it is possible to use combinations of these light sources, optical filters and optical components to collimate and guide light. It is also possible to use combinations of these light sources and optical fibers. In case of using an incoherent light source as a light source, it is preferable to combine it with optical filters.

In the present invention, it is possible to use a combination of a single or a plurality of sensing elements with a light source having a different wavelength in order to improve the sensitivity and dynamic range of the sensor.

A light source and a photodetector to be used in the present invention may be an integrated device including both a light source and a photodetector detecting light from said light source. As such a light-source/photodetector integrated device can be generally used a photoreflector, a reflection photosensor, a reflection photointerrupter and a light reflector IC. Or alternatively, the integrated device may be a photosensor unit in which an LED and a diode photodetector/phototransistor are arranged on the same side. According to such a photosensor unit, reflection from the sensing film disposed in front of a light-emitting diode and a photodetector can be detected. Further, in addition to the above the integrated device may contain an amplifier for amplifying signals and an electronic circuit for signal processing device. Hence, the sensor of the present invention may comprise a sensing element, an integrated device including a light source and a photodetector, and electronic circuitry.

In another preferred embodiment of the present invention, the polarizer 4 may be positioned downstream of the site where the incident light is reflected by the sensing element 1. In still another preferred embodiment, the polarizer 4 and the beam splitter 3 may be replaced by a polarizing beam splitter. The use of a polarizing beam splitter offers the advantage that perpendicularly polarized light is launched into the optical path for signal light while parallel polarized light is launched into the optical path for reference light 5.

The quantity of light reflected by the thin film on the substrate is determined not only by the incident angle of the light and the degree of its polarization but also by the thickness of the thin film, its refractive index and the refractive indices of the media above and below the thin film. The light reflected from the surface of the thin film interferes with the light reflected at the interface between the thin film and the substrate. This phenomenon of light interference is largely dependent on the thickness and refractive index of the thin film.

Another embodiment of the present invention is shown in FIG. 9A. FIG. 9A shows a cross sectional view of an optical sensor device having a series of sensing elements 1 (comprising thin film 7 formed on substrate 8) and photoreflectors 12 (each having both a light source and a photodetector) for simultaneous detection of different chemical species within a sample stream 13. Light is emitted from each photoreflector 12 toward a corresponding sensing element 1, wherein each sensing element 1 can be made from similar or dissimilar materials. The emitted light is reflected off each sensing element 1 to the photodetector of the corresponding photoreflector 12.

Thus, a plurality of chemical species in sample stream 13 can be simultaneously detected and distinguished from each other by measuring the change in the intensity of reflected light or response time that occurs as a result of the swelling of the thin film 7 or the change in the thin film 7 optical parameters for each sensing element 1.

FIG. 9B shows a plane view of a single photoreflector 12 having both a light source 2 and a photodetector 9 for detecting light from the light source reflected from a corresponding single sensing element 1 of FIG. 9A.

Figure 2:
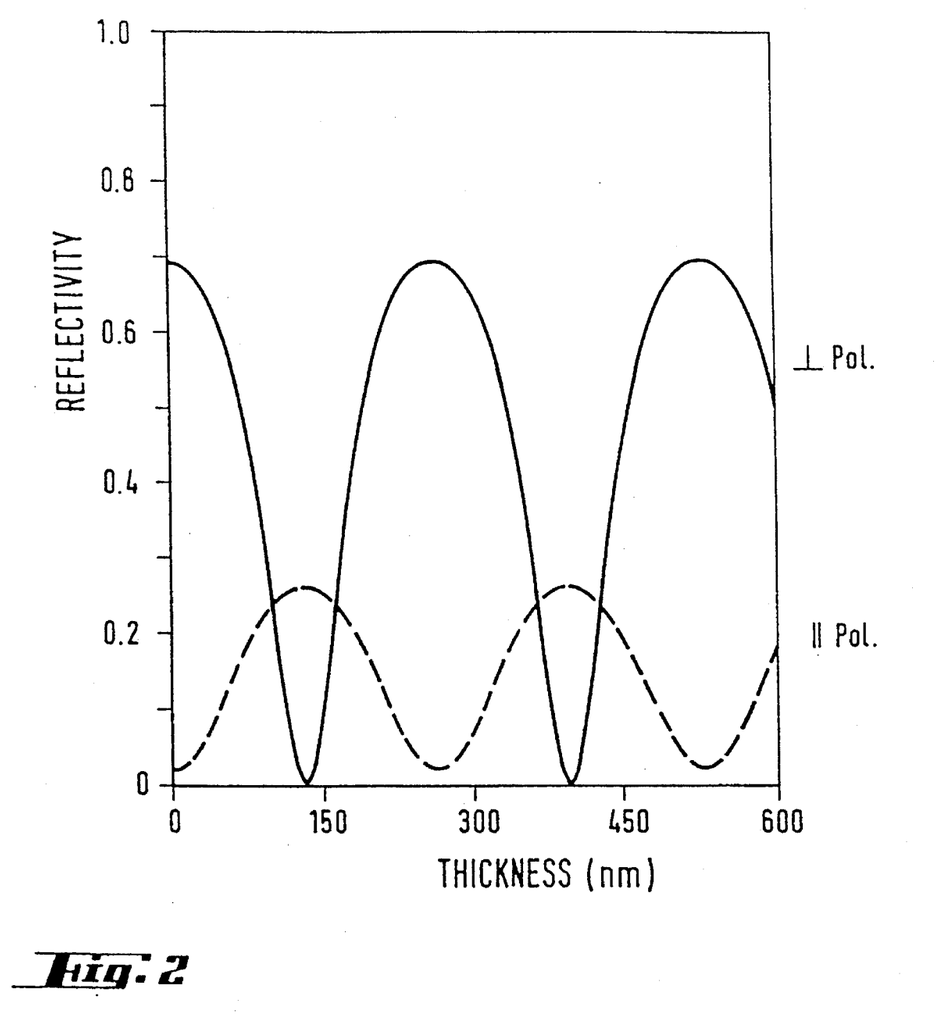
FIG. 2 is a graph showing the relationship between reflectance and the thickness of a thin film for both S and P polarization.

FIG. 2 is a graph showing the results of calculation of the relationship between the thickness of a thin film and the reflectance of light incident on the film. The thin film used in the experiment had a refractive index of 1.522 and it was supported on a silicon substrate. The incident light was polarized either parallel or normal to the plane of incidence and the angle of incidence was 70°. The incident light had a wavelength of 633 nm. As is clear from FIG. 2, incident light polarized normal to the plane of incidence was much more sensitive to the film thickness than parallel polarized incident light. It is therefore preferred to use normal polarized incident light rather than parallel polarized incident light in the present invention. Needless to say, unpolarized light may be used as incident light but it should be noted that the use of unpolarized incident light tends to result in a lower sensitivity of measurement.

In the present invention, light may be split, guided or collected or collimated on the sensing element or photodetectors by means of appropriate optical members and fiber optics.

The present invention has been accomplished on the basis of the fact that the thin film in the sensing element reacts with or absorbs or adsorbs a chemical species to thereby experience a change in either the thickness or refractive index of the film or changes in both factors. Using the IER technique, such change or changes are measured as corresponding changes in reflected light, whereby the chemical species of interest is checked for its presence and/or its quantity is detected. The thin film to be used for this purpose in the present invention may be composed of any organic and polymer materials that are capable of various interactions (e.g. reaction, adsorption and absorption) with the chemical species to be detected. Examples of such materials include vinyl polymers having various side-chain groups, as well as polysiloxanes and polycondensation products (e.g. polyesters, polyamides, polyimides, polyurethanes and polyureas).

From the viewpoint of sensitivity, a homopolymer or a copolymer having the following recurring unit (I) can be preferably used:

wherein

X represents —H, —F, —Cl, —Br, —$CH_3$, —$CF_3$, —CN or $CH_2$—$CH_3$;

$R^1$ represents —$R^2$ or —Z—$R^2$;

Z represents —O—, —S—, —NH—, $NR^2$—, —$NR^2$—, —(C=Y)—, —(C=Y)—Y—, —Y—(C=Y)—, ($SO_2$)—, —Y'—($SO_2$)—, —($SO_2$)—Y'—, —Y'—($SO_2$)—Y'—, —NH—(C=O)—, —(C=O)—NH—, —(C=O)—$NR^{2'}$—, —Y'—(C=Y)—Y'— or —O—(C=O)—($CH_2$)$_n$—(C=O)—O—;

Y represents independently O or S;

Y' represents independently O or NH;

n represents an integer of 0 to 20; and $R^2$ and $R^{2'}$ represents independently, a straight-chain alkyl group, branched-chain alkyl group, cycloalkyl group, unsaturated hydrocarbon group, aryl group, saturated or unsaturated hetero ring or derivatives thereof.

Particularly preferably used is a homopolymer or copolymer having the above recurring unit (I):

wherein

X represents H or $CH_3$;

$R^1$ represents a substituted or unsubstituted aryl group or —Z—$R^2$;

Z represents —O—, —(C=O)—O— or —O—(C=O)—; and $R^2$ represents a straight-chain alkyl group, a branched-chain alkyl group, a cycloalkyl group, an unsaturated hydrocarbon group, an aryl group, a saturated or unsaturated hetero ring or substituents thereof.

More preferably used are: poly(methyl methacrylate); poly(isodecyl methacrylate); poly(2-ethylhexyl methacrylate-co-styrene); poly(ethylhexyl methacrylate); poly(methyl methacrylate-co-2-ethylhexyl acrylate); poly(methyl methacrylate-co-2-ethylhexyl methacrylate); poly(cyclohexyl acrylate); poly(dodecyl methacrylate); poly(vinyl propionate); poly(benzyl methacrylate-co-2-ethylhexyl methacrylate); poly(2-ethylhexyl methacrylate-co-glycidyl methacrylate); poly(butyl methacrylate); and poly(tetrahydrofurfuryl methacrylate).

Besides these polymers, compounds of low molecular weights can also be used and they include, for example, phthalocyanides, prphines, prhyrins, organometallic complexes, chelating agents (e.g. crown compounds such as cyclodextrins, calixarenes, crown ethers and azacrowns), and cryptands. Inorganic substances such as metal oxides and sulfides can also be used to make the substrate. Exemplary inorganic substances include $SiO_2$, $TiO_2$, $Al_2O_3$ and ZnS. these substances may be used in aerogel and various other forms.

The thin film in the sensing element to be used in the present invention may have a multilayer structure, as exemplified by the combination of a $SiO_2$ layer with an organic or high-polymer layer. The organic or high-polymer layer is formed on the $SiO_2$ layer and functions as a detector of chemical species.

The substrate for supporting the thin film may be formed of transparent glass or highly reflective material such as a semiconductor or a metal. A glass substrate or other substrates that carry metal or semiconductor films may also be used. Highly reflective materials are preferred substrate materials since they are more reflective than glass and, hence, provide a higher sensitivity and a broader dynamic range. On the other hand, the use of a transparent substrate such as a glass substrate has the advantage that light can be admitted onto the thin film from the side facing the substrate. As a result, the optical path of incident light can be kept apart from the chemical species to be detected. This advantage proves to be the most effective in the case of detecting non-transparent (opaque or translucent) chemical species.

The thin film in the sensing element to be used in the present invention may be formed by any known thin film processes, such as spin coating, the casting of solutions of film-forming materials in solvents, vapor-phase deposition and other evaporation techniques.

For a given angle of incidence, the thin film has an optical thickness which depends on its reactive index. Typically, the optimal value is selected from those which provide large S/N ratios, for achieving a higher sensitivity and a faster response time, the thin film has preferably a thickness of 1 µm and below.

The sensor of the present invention has many advantages: first, the light source, detectors and other necessary components need not be of any special types and, hence, the sensor has a very simple construction and can be manufactured at low cost; second, the equipment is small in size; third, the thin film can be formed on a flat substrate very easily compared to the prior art sensor that has the thin film formed at an end of an optical fiber; fourth, a very thin film can be formed on the substrate and this contributes to higher sensitivity and a faster response time.

The following examples are provided for the purpose of further illustrating the present invention but are in no way to be taken as limiting.

EXAMPLE 1

Determining optimal values for the thickness of thin film and the angle of incidence.

As FIG. 2 shows, the intensity of light reflected from a thin film is a periodic function of the film thickness. If the substrate is made of silicon, the condition for the intensity of reflected light to assume a maximum and a minimum value in the case of S polarization is expressed by the following equation:

$$4nd_m \cos\theta/\lambda = m \ (m=0,1,2)$$

If m is an even number the intensity of reflected light is at maximum and if m is an odd number, the intensity is at minimum. In the above equation, λ designates the wavelength of incident light, n the refractive index of the thin film, θ the angle of light propagation through the thin film, and dm the thickness of the film.

To achieve quick response, the thickness of the film is preferably small. The condition of primary reflection for the intensity of reflected light to be at minimum is that the thickness of the film satisfy the following relation:

$$d_1 = \lambda/4n \cos\theta$$

If the thin film is made of poly(2-ethylhexyl methacrylate-co-styrene) and if the angle of incidence is 70°, the film thickness is 132.1 nm since n=1.522.

Figure 3:
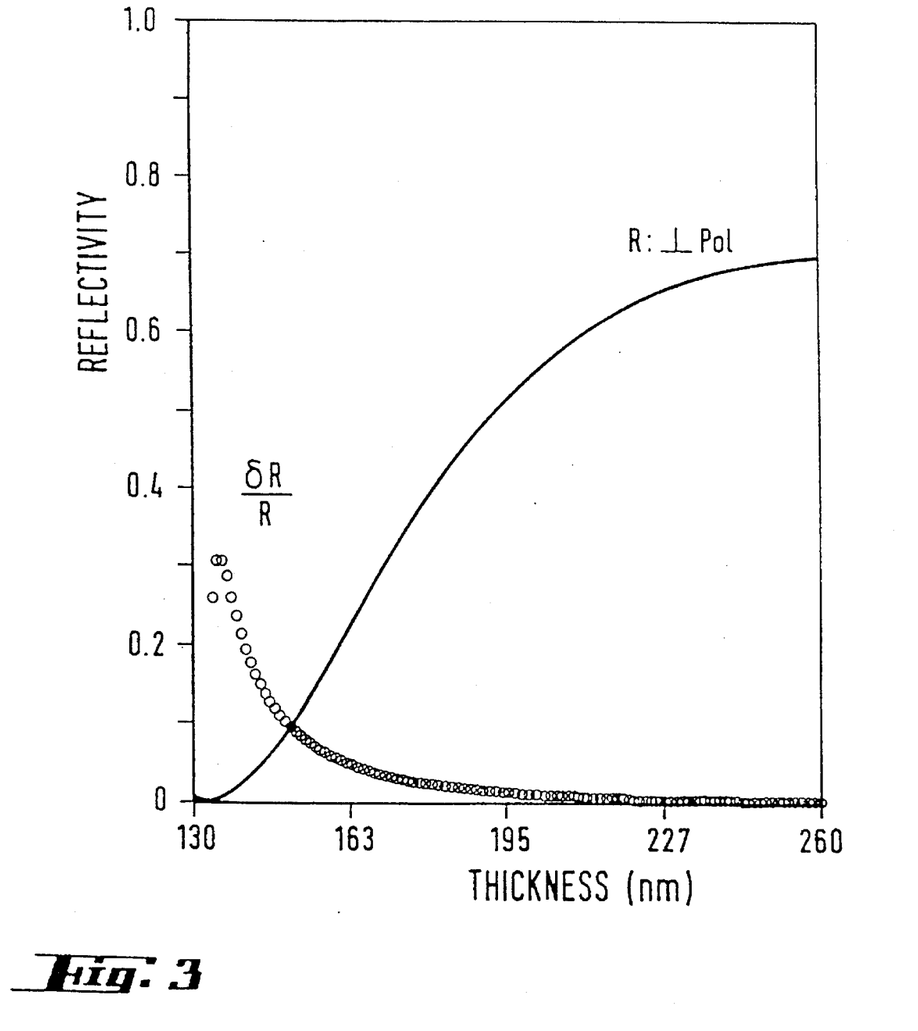
FIG. 3 is a graph showing the relationship between the reflectance of S-polarized light, the change in reflectance and the thickness of a thin film.

The sensitivity of measurement is determined by the change in reflectance R (i.E., δR/R). FIG. 3 shows the calculated values of reflectance R and its change δR/R for the case of using a sensing element made from the combination of thin film of poly(2-ethylhexyl methacrylateoco-styrene) with a silicon substrate. Obviously, δR/R peaks at d=135 nm. It was therefore preferably that the thin film in the sensing element under consideration should have a thickness of 135 nm.

Figure 4:
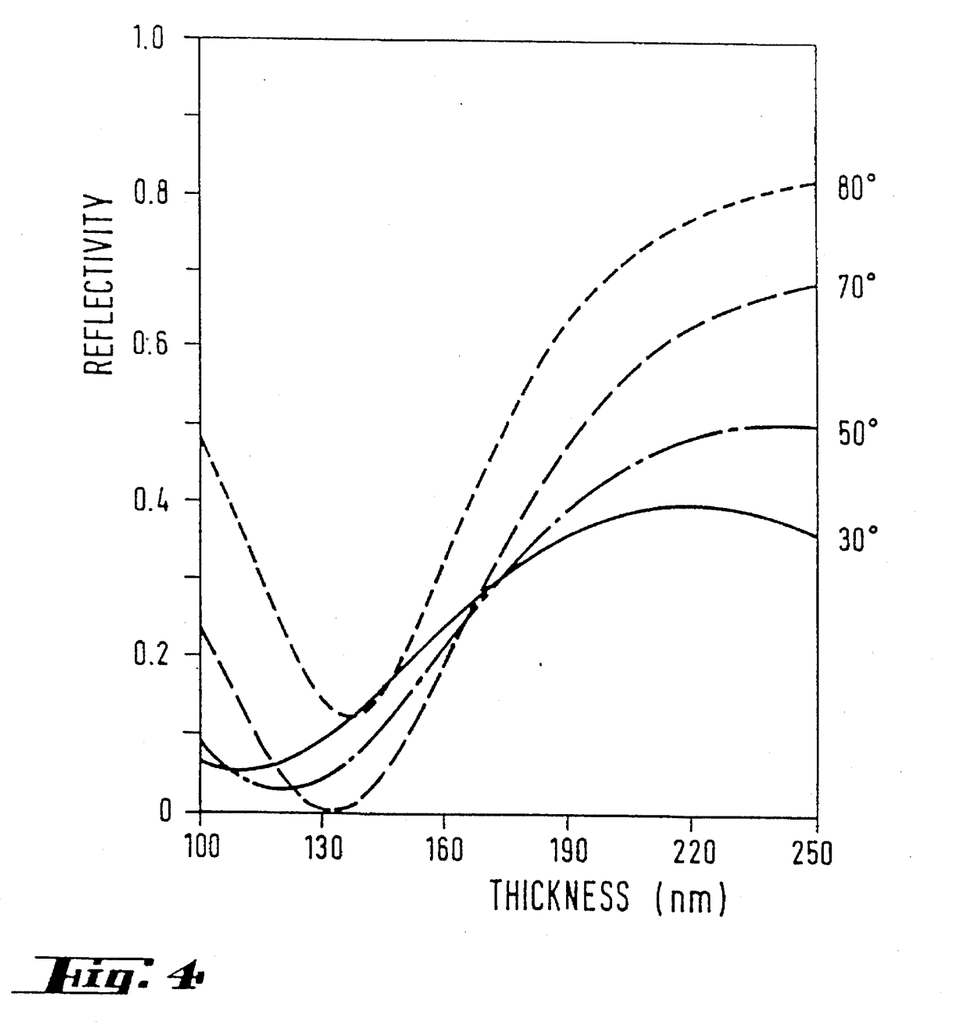
FIG. 4 is a graph showing the relationship between reflectance and the thickness of a thin film for varying angles of incidence.

The relationship between reflectance R and incident angle for the sensing element made from the combination of a thin film of poly(2-ethylhexyl methacrylate-co-styrene) with a silicon substrate is shown in FIG. 4, from which one can see that δR/R, or the gradient of R, increases with the incident angle. However, as far as the sensitivity (δR/R) is concerned, the incident angle is preferably 70° or so.

EXAMPLE 2

Measurement by IER

Measurements were conducted at room temperature using equipment having the layout shown in FIG. 1. S-polarized light from a He—Ne laser was divided by a beam splitter into reference light and signal light. The laser light had a wavelength of 832.8 nm. The signal light was allowed to be indicant on the thin film in the sensing element. The reference light was supplied to the associated photodetector, where it was converted to an electric signal $I_R$. On the other hand, the signal light as reflected by the sensing element was supplied to the associated photodetector, where it was converted to an electric signal $I_S$. The two electric signals were compared in electronic circuitry and the result was delivered as output from a personal computer.

The sensing element was composed of a thin film of poly(dodecyl methacrylate) on a silicon substrate and it was prepared by the following procedure: poly(dodecyl methacrylate) was dissolved in cyclohexanone to make a 10 wt % solution, which was spin coated onto the silicon substrate. The thickness of the polymer film was adjusted by varying the rotating speed of the silicon substrate. The thus formed polymer films of varying thicknesses were dried in a vacuum-drying furnace at temperatures in the neighborhood of the glass transition point of the polymer. The film thickness was measured by a stylus method with a surface texture analyzing system Model 3030 ST of DEKTAK Corp. The films had thicknesses in the range from about 100 to about 300 nm.

For measurements by IER, the sensing element was placed in a flow cell, through which gaseous, vaporized or liquid samples could be admitted. The incident angle of laser light was set to lie between 56 and 70° depending upon the thickness of the polymer film.

Figure 5:
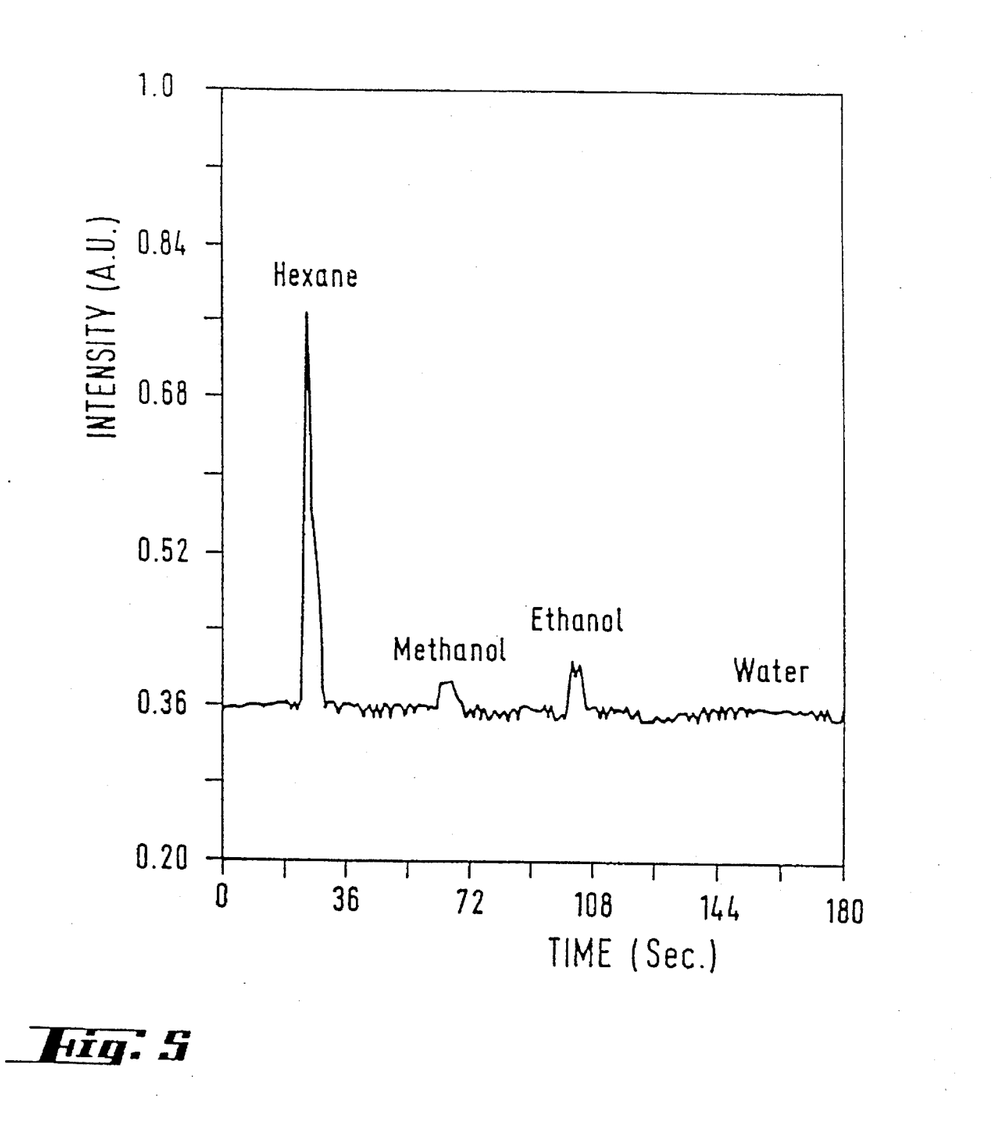
FIG. 5 is a graph showing the sensitivities to various chemical species as detected on a thin film of poly(lauryl methacrylate)

FIG. 5 shows the results of measurements by IER on the vapors of hexane, methanol, ethanol and water that were admitted through the flow cell. The polymer film had a thickness of 135 nm and the laser light was allowed to be incident at 70°. As FIG. 5 shows, the thin film of poly(dodecyl methacrylate) was responsive to hexane with a very high sensitivity but its sensitivity to methanol and ethanol was low. The film was practically insensitive to water.

One can also see from FIG. 5 that the thin film of poly(dodecyl methacrylate) responded to hexane very quickly. In Example 2 under consideration, data were sampled at intervals of 1 sec. In view of the fact that a 124% relative change in the intensity of reflected light was recorded at one sampling (i.,e. one second), the sensor of the present invention features very quick response.

EXAMPLE 3

Detecting the vapors of various chemical species with different thin films

Various polymers were processed into thin films, which were used to make sensing elements according to the present invention. the polymers used were: Poly(vinylpyrrolidone), PVP:poly(vinyl propionate), PVPr:poly(vinyl acetate), PVAc: polystyrene, PST: poly(dodecyl methacrylate), PDDMA: and poly(butyl methacrylate), PBMA.

Thin films were formed from these polymers by the following procedure. First, the polymers were dissolved in a suitable solvent, say, cyclohexanone to prepare solutions at concentrations of 5–10 wt %. The solutions were spin coated onto silicon substrates to form thin films, which were then dried in a vacuum-drying furnace for about 1.5 hours at temperatures in the neighborhood of the glass transition points of the respective polymers. The thicknesses of the dried films were measured by the same method as in Example 2. To improve the detection sensitivity, the film thickness should be no more than 1 μm and in Example 3 under consideration, all the films used were 135 nm thick.

For measurements by IER, the sensing element was placed in a flow cell, through which the vapors of various hydrocarbons could be admitted together with air or nitrogen. The vapors of hydrocarbons to be detected were prepared by bubbling air or nitrogen through the hydrocarbons in a liquid state. The hydrocarbons used in Example 3 were toluene, hexane, methanol and ethanol. Water was also used as a species to be detected.

Light from a He—Ne laser (λ, 632.8 nm) was applied to each of the thin films at an incident angle of 70°. The laser light had been polarized linearly in a direction normal to the plane of incidence. The intensity of reflected light from the thin films was measured with the associated photodetector, whose output was recorded on a chart recorder and a personal computer (Compaq 388 PC).

The results of measurements are shown in Table I in terms of "sensitivity", which is the percentage of the change in the intensity of reflected light as divided by the absolute value of the same intensity. As is clear from Table I, the sensitivity of measurement varied with the kinds of thin film and hydrocarbons to be detected.

TABLE I

| Polymer | Toluene | Hexane | Methanol | Ethanol | Water |
| --- | --- | --- | --- | --- | --- |
| PVP | 30.0 | 6 | 9.5 | 16.0 | 24.5 |
| PVPr | 46.8 | 14 | 14.1 | 17.2 | 1.4 |
| PVAc | 2.0 | 6.3 | 22.6 | 9.4 | 12.5 |
| PSt | 2.7 | <1.0 | 6.6 | 6.3 | 6.0 |
| PDDMA | 115.9 | 124.3 | 10.0 | 14.3 | 0.6 |
| PBMA | 59.1 | 38.5 | 9.5 | 20.8 | 5.7 |

EXAMPLE 4

Detecting different chemical species with more than one sensor

A plurality of chemical species can be distinguished from each other or detected simultaneously by means of a plurality of series of sensing elements.

As Table I in Example 3 shows, the thin PVP film has high sensitivity to toluene and water but its sensitivity to hexane is low. On the other hand, the thin PDDMA film has high sensitivity to toluene and hexane but is substantially insensitive to water. Therefore, it is not easy to detect those chemical species as distinguished from each other by using the thin PVP and PDDMA film individually. In Example 4 under consideration, both thin films were formed on one silicon substrate to provide two channels of measurement and the intensity of reflected light was measured at room temperature for each independent channel. By comparing the measured intensities of reflected light, toluene, hexane and water could be identified simultaneously.

EXAMPLE 5

Detecting gasoline and diesel oil

Gasoline and diesel oil were detected with equipment having the same construction as in Example 3. The sensing element was composed of a thin film of poly(methyl methacrylate-co-butyl methacrylate) on a silicon substrate and it was formed by the following procedure: poly(methyl methacrylate-co-butyl methacrylate) was dissolved in cyclohexane to make a 10 wt % solution, which was spin coated on the silicon substrate. The polymer film thus formed had a thickness of 131 nm. Light from a He—Ne laser was admitted onto the film at an incident angle of 70°. The result of detection with this sensing element is shown in FIG. 6.

Figure 6:
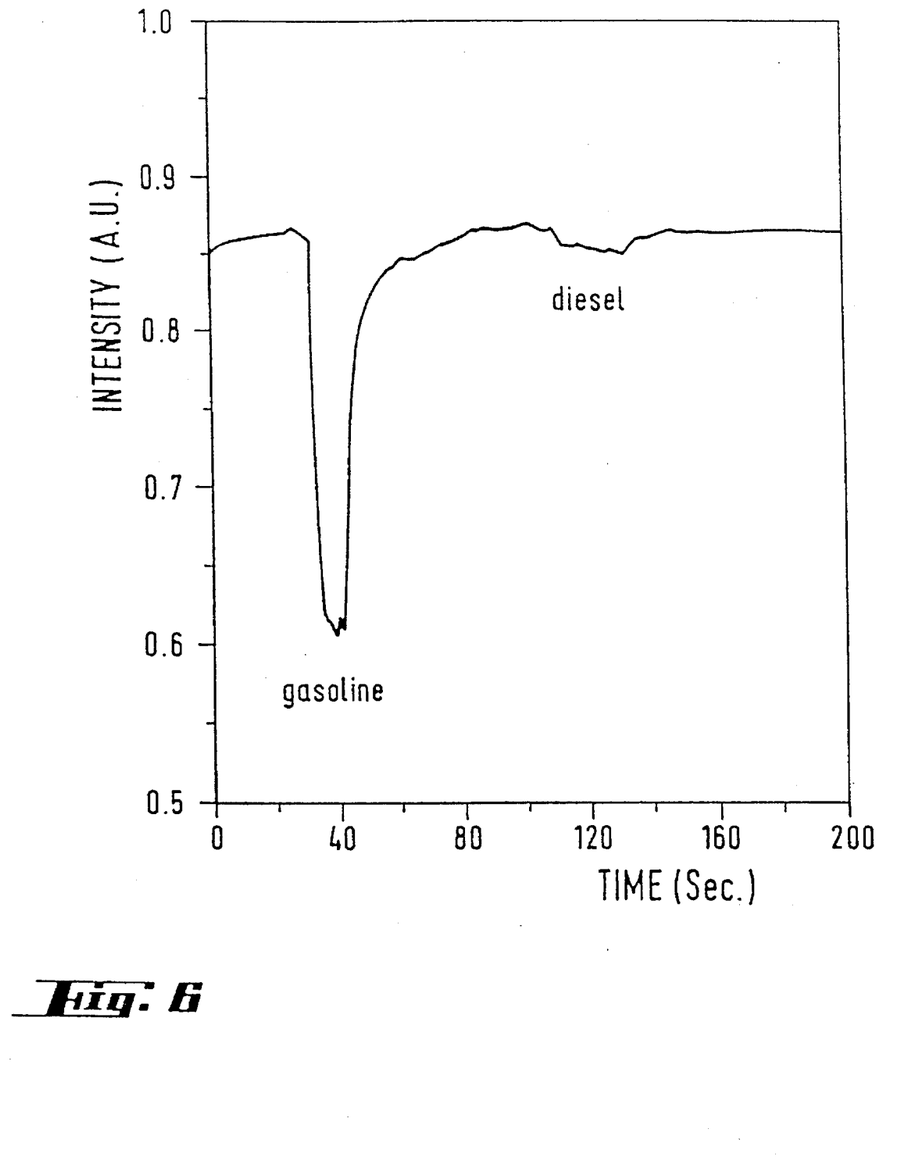
FIG. 6 is a graph showing the sensitivities to gasoline and diesel oil as detected on a thin film of poly(methyl methacrylate-co-butyl methacrylate)

As is clear from FIG. 6, the thin film of poly(methyl methacrylate-co-butyl methacrylate) has high sensitivity to gasoline but very low sensitivity to diesel oil. Therefore, using this film, one can detect gasoline and diesel oil as distinguished from each other.

EXAMPLE 6

Detecting gasoline and diesel oil with a photoreflector

Figure 7:
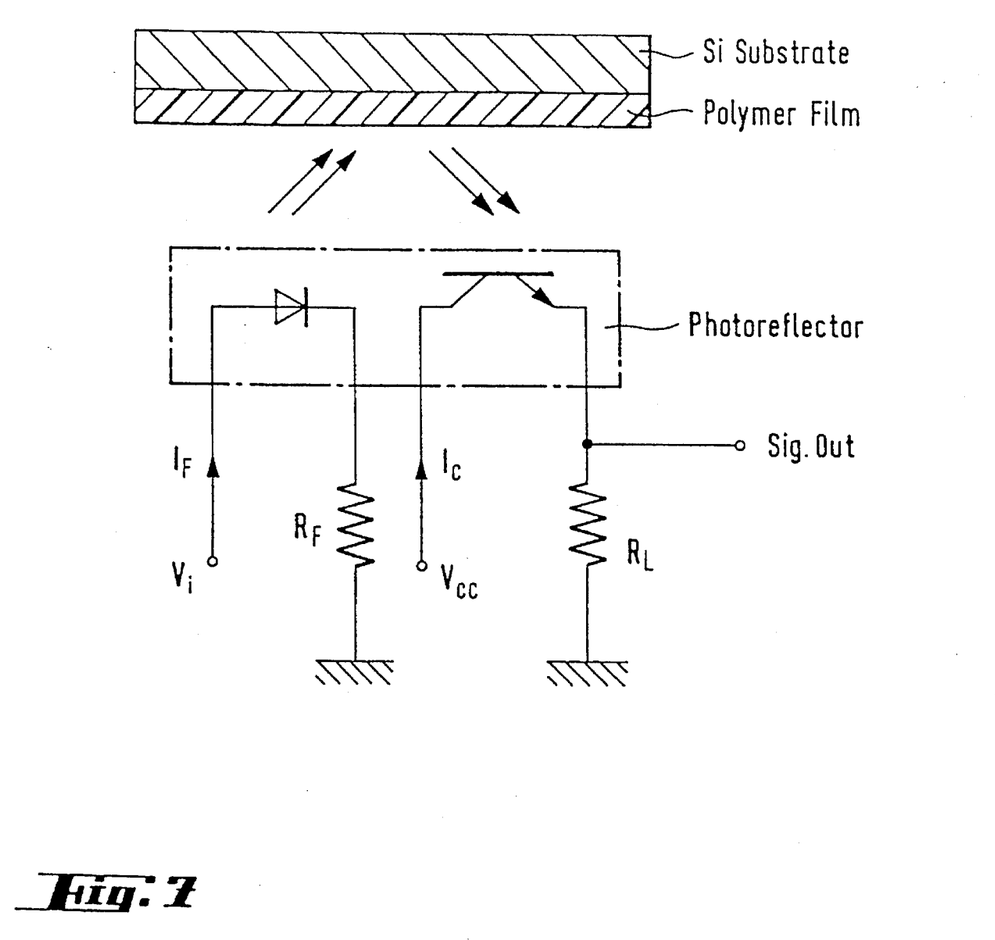
FIG. 7 shows the equipment using s photoreflector.

In FIG. 7 is shown the arrangement of n detection system of a sensor with a photoreflector. A film of poly(benzyl methacrylate-co-2oethylhexyl methacrylate) was formed on a silicon substrate by means of spin coating. This polymer film had a thickness of 420 nm and a refractive index of 1.53. The silicone substrate coated with this polymer film was provided in front of a Photoreflector P2826 manufactured by Hamamatsu Photonics. The distance was 3 mm. The light from a light-admitting diode is reflected upon the polymer film and detected by means of a phototransistor in the Photoreflector P2826. The light source of the Photoreflector P2826 was a gallium-arsenic emission diode, whose peak wavelength was about 940 nm and half-value width was 50 nm. The photodetector of the Photoreflector P2826 was a silicone phototransistor.

Figure 8:
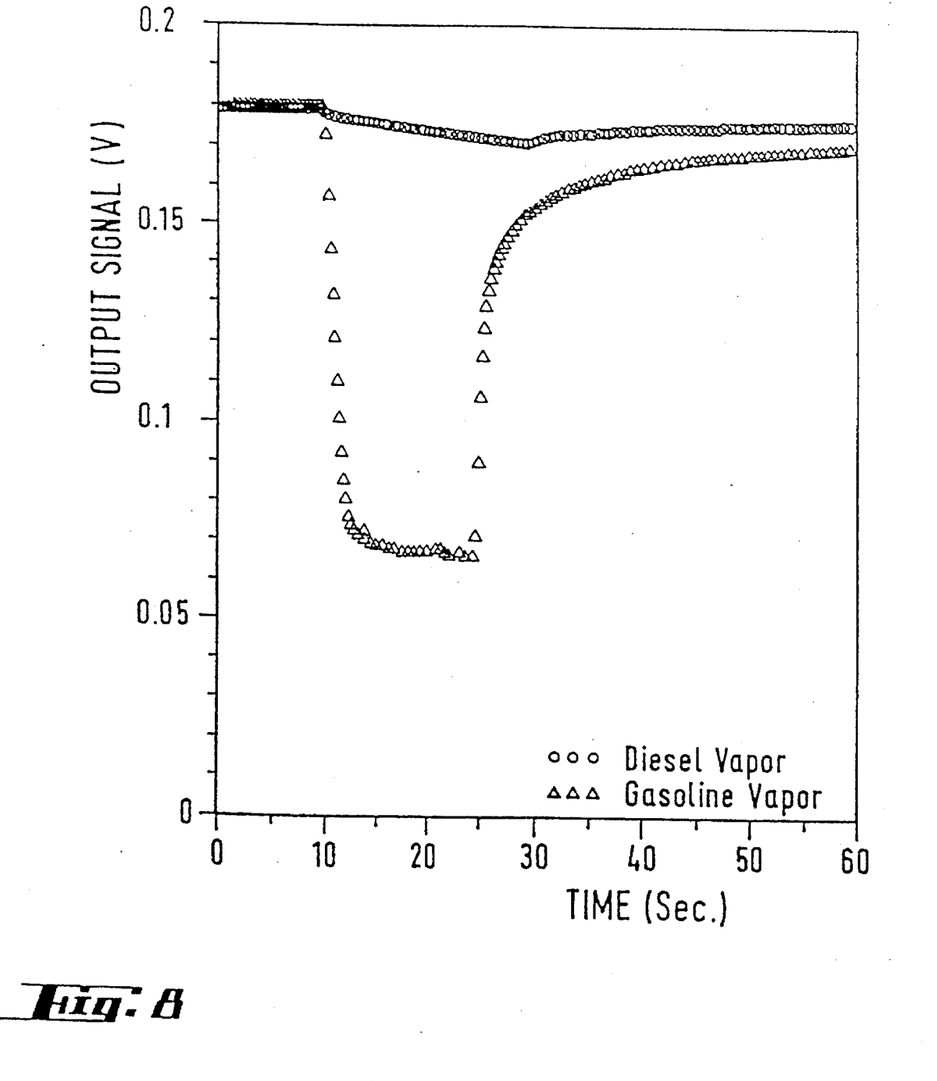
FIG. 8 shows the sensitivities to vapors of gasoline and diesel oil in case of using a thin film of poly(benzyl methacrylate-co-2-ethylhexyl methacrylate)

In FIG. 8 are shown output signals of gasoline vapor and diesel vapor. The vapors were flowed between the photoreflector and the silicone substrate coated with the polymer film.

As is clear from FIG. 8, the thin film of benzyl methacrylate-co-2-ethylhexyl methacrylate has low sensitivity to diesel oil but high sensitivity to gasoline. Therefore, using this film, it is possible to detect gasoline and diesel oil as distinguished from each other.

What is claimed is:

1. An optical sensor for detecting gaseous or liquid chemical species comprising:

a sensing element having a single flat light reflecting substrate and at least one transparent thin film selected from the group consisting of organic film and inorganic film formed on said substrate; and means for measuring, by interference enhanced reflection, a change in light reflection characteristic of the sensing element occurring as a result of the thin film reacting with or absorbing or adsorbing the chemical species to be detected.

2. The optical sensor according to claim 1, wherein the means for measuring detects swelling of the thin film caused by the thin film reacting with or absorbing or adsorbing the chemical species to be detected.

3. The optical sensor according to claim 1, wherein the means for measuring detects a change in the thin film thickness or refractive index or the changes in both parameters caused by the thin film reacting with or absorbing or adsorbing the chemical species to be detected.

4. The optical sensor according to claim 1, wherein the means for measuring further includes means for detecting a change in the product of the thickness and refractive index of the thin film.

5. The optical sensor according to claim 1, wherein the transparent thin film is a high polymer film.

6. The optical sensor according to claim 1, wherein the means for measuring detects a change in the intensity of reflected light to determine the presence of the chemical species.

7. The optical sensor according to claim 1, wherein the means for measuring detects a change in the intensity of reflected light to determine the quantity of the detected chemical species.

8. The optical sensor according to claim 1, wherein the means for measuring detects a plurality of chemical species as distinguished from each other by measuring the change in the intensity of reflected light or response time.

9. The optical sensor according to claim 8, wherein the means for measuring further includes a series of sensing elements that are made of similar or dissimilar materials for simultaneous detection and identification of different chemical species.

10. The optical sensor according to claim 1, wherein the means for measuring comprises means for emitting light;

means for dividing the emitted light into a reference light beam and a detection light beam;

means for detecting the reference light beam and generating a reference signal proportional to the intensity of the reference light beam;

means for polarizing the detection light beam in a direction normal to the plane of the sensing element;

means for detecting the reflection light beam generated by the polarized detection light beam reflected from the sensing element and generating a reflection signal proportional to the intensity of the reflection light beam; and means for receiving the reference and reflection signals, and outputting a measurement signal based on ratio between the reference and reflection signals, whereby said measurement signal is use to detect the presence and/or quantity of chemical species.

11. The optical sensor according to claim 1, wherein the means for measuring comprises means for emitting and receiving light having a means for generating signals proportional to the intensity of the received light;

means for dividing the emitted light into a reference light beam and a detection light beam;

said means for emitting light and receiving light receiving the reference light beam and generating a reference signal proportional to the intensity of the reference light beam;

means for polarizing the detection light beam in a direction normal to the plane of the sensing element;

said means for emitting and receiving light receiving the reflection light beam generated by the polarized detection light beam reflected from the sensing element and generating a reflection signal proportional to the intensity of the reflection light beam; and means for receiving the reference and reflection signal, and outputting a measurement signal based on ratio between the reference and reflection signal, whereby said measurement signal is use to detect the presence and/or quantity of chemical species.

12. The sensor of claim 11 wherein the thin film has a thickness other that $\lambda/4$, or a multiple of this dimension, wherein $\lambda$ is a wavelength of incident light applied to the thin film.

* * * * *

UNITED STATES PATENT AND TRADEMARK OFFICE
CERTIFICATE OF CORRECTION

PATENT NO. : 5,563,707
DATED : October 8, 1996
INVENTOR(S) : Prass et al.

It is certified that error appears in the above-indentified patent and that said Letters Patent is hereby corrected as shown below:

Column 14, claim 12, line 10, change "that" to --than--

Signed and Sealed this

Second Day of December, 1997

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,563,707
DATED : October 8, 1996
INVENTOR(S) : Prass et al.

It is certified that error appears in the above-identified patent and that said Letters Patent is hereby corrected as shown below:

ON THE COVER PAGE:

Beneath UNITED STATES PATENT [19], change "Prass et al." to --Liu et al.--.

Under [75] Inventors, change the order to --Yuan Liu, Kawagoe, Japan; Werner Prass, Mainz; Thomas Stehlin, Hofheim/Taunus, both of Germany; Shizuo Ogura, Tsurugashima, Japan; Kenji Motosugi, Kawagoe, Japan; Akihiko Tokida, Kawagoe, Japan; Tetsu Yamamoto, Kawagoe, Japan--.

Signed and Sealed this

Nineteenth Day of May, 1998

Attest:

BRUCE LEHMAN

Attesting Officer

Commissioner of Patents and Trademarks